(12) United States Patent
Holm et al.

(10) Patent No.: US 9,878,145 B2
(45) Date of Patent: Jan. 30, 2018

(54) APPARATUS INCLUDING A CONDUIT CLAMPING DEVICE

(71) Applicant: DENTSPLY International Inc., York, PA (US)

(72) Inventors: Niels Erik Holm, Birkerød (DK); Erik Andréen, Göteborg (SE); Bengt Daniel Envall, Herrljunga (SE)

(73) Assignee: DENTSPLY International Inc., York, PA (US)

( * ) Notice: Subject to any disclaimer, the term of this patent is extended or adjusted under 35 U.S.C. 154(b) by 254 days.

(21) Appl. No.: 14/522,736

(22) PCT Filed: Apr. 24, 2013

(86) PCT No.: PCT/EP2013/058554
§ 371 (c)(1),
(2) Date: Oct. 24, 2014

(87) PCT Pub. No.: WO2013/160380
PCT Pub. Date: Oct. 31, 2013

(65) Prior Publication Data
US 2016/0114148 A1    Apr. 28, 2016

(30) Foreign Application Priority Data
Apr. 24, 2012   (DK) ................................ 2012 00282

(51) Int. Cl.
*A61M 39/28*    (2006.01)
*A61M 1/00*    (2006.01)
(Continued)

(52) U.S. Cl.
CPC ........ *A61M 39/284* (2013.01); *A61M 1/0023* (2013.01); *A61M 1/0045* (2014.02);
(Continued)

(58) Field of Classification Search
CPC .............. A61M 39/284; A61M 1/0045; A61M 1/0023; A61M 5/14; A61M 5/16813; A61M 39/28
(Continued)

(56) References Cited

U.S. PATENT DOCUMENTS 2,113,022 A * 4/1938 Hefti ...................... B65D 35/40
222/101
2,309,302 A   9/1941 Butler et al.
(Continued)

FOREIGN PATENT DOCUMENTS

GB          2352797 A        2/2001

OTHER PUBLICATIONS

International Search Report PCT/EP2013/058554.

*Primary Examiner* — Manuel Mendez
(74) *Attorney, Agent, or Firm* — Perkins Coie LLP (57) ABSTRACT

An apparatus comprising a conduit clamping device with a closing mechanism for closing and opening passage of fluid or air in a flexible conduit is disclosed. The apparatus comprises a movable arm or disk that is connected to a manipulation arm or a knob; a conduit in form of a tube, that is laid flat against an abutment or protrusion; and a guide structure that constrains the movable arm or disk between the guide structure and the tube and being designed such that movement of the arm or disk will control the compression of the tube.

25 Claims, 8 Drawing Sheets

(51) Int. Cl.
  *A61M 5/14* (2006.01)
  *A61M 5/168* (2006.01)

(52) U.S. Cl.
  CPC .......... *A61M 5/14* (2013.01); *A61M 5/16813* (2013.01); *A61M 39/28* (2013.01); *A61M 1/0064* (2013.01)

(58) Field of Classification Search
  USPC ............ 604/178, 214, 234, 246–250, 30–34, 604/167.03; 137/594; 251/9, 8
  See application file for complete search history.

(56) References Cited

U.S. PATENT DOCUMENTS

| | | | |
|---|---|---|---|
| 3,419,245 A | 12/1968 | Scola | |
| 3,915,167 A * | 10/1975 | Waterman | A61M 39/284 251/9 |
| 4,053,135 A | 10/1977 | Saliaris | |
| 4,369,951 A | 1/1983 | Marsoner et al. | |
| 4,376,439 A | 3/1983 | Lauterjung | |
| 4,435,170 A | 3/1984 | Laszczower | |
| 4,570,829 A * | 2/1986 | Allen | B65D 35/40 222/181.2 |
| 4,643,389 A | 2/1987 | Elson et al. | |
| 5,147,292 A * | 9/1992 | Kullas | A61M 1/0064 601/161 |
| 5,230,704 A * | 7/1993 | Moberg | A61M 1/0064 604/250 |
| 6,196,519 B1 | 3/2001 | Utterberg | |
| 7,178,699 B2 * | 2/2007 | Spray | B67D 1/1405 222/212 |
| 8,702,681 B2 * | 4/2014 | Douglas | A61M 39/22 137/15.23 |
| 9,463,968 B2 * | 10/2016 | Schaefer | B67D 3/041 |
| 2005/0107757 A1 | 5/2005 | Burton et al. | |
| 2006/0264995 A1 | 11/2006 | Fanton et al. | |
| 2008/0146991 A1 | 6/2008 | Hernandez et al. | |

* cited by examiner

APPARATUS INCLUDING A CONDUIT CLAMPING DEVICE

CROSS-REFERENCE TO RELATED APPLICATIONS

This is a national phase application of International Application Ser. No.: PCT/EP2013/058554, filed on Apr. 24, 2013, which claims the benefit of and priority to DK Patent Application Ser. No. 2012 00282, filed on Apr. 24, 2012, which are herein incorporated by reference for all purposes.

TECHNICAL FIELD

The present invention relates to an apparatus comprising a conduit clamping device with a closing mechanism, and in particular to such an apparatus which can be used in an apparatus for removal and supply of fluid or air, below skin level, at a human or an animal. The apparatus may in addition comprise a hypodermic needle for penetration of the skin and a suction and collection device for suction of the fluid through the hypodermic needle, or a drain tube or a catheter. The apparatus is preferably adapted for removal of e.g. accumulations of fluid or air being a result of e.g. surgery, or solely accumulations of fluid in e.g. knees or other tissue with cavity or in regions of organs, e.g. gastrointestinal regions or in the heart/lungs. Additionally or alternatively, the apparatus may have access for adding fluid to the cavity with the purpose of infusion of medicine in the cavity or performing lavage of preformed cavity or as a result of prior surgery. However, the conduit clamping device is also useable in other medical appliances, such as in irrigation systems, e.g. for rectal irrigation or bladder irrigation.

BACKGROUND OF THE INVENTION

Accumulation of fluid below a surgical wound appears after various types of surgery, especially after surgery for breast cancer. However, accumulations of fluid appears also frequently after vascular surgery, e.g. in the inguinal region. Patients with arthritis often have accumulation of fluid in there joints caused by the disease e.g. in the knees.

Furthermore, accumulations of fluid may appear in the lungs, around the heart, or as an abscess connected to any organ under the skin e.g. in case of infectious diseases.

Accumulations of fluid in the lungs or in the abdominal cavity also often appear in patients suffering from severe cancer. When emptying accumulations of fluid in such cases various systems are used today, inter alia just a hypodermic needle mounted on a syringe or various joint systems with three-way taps, hoses, hypodermic needles, drain tubes, catheters and syringes. If an outlet hose has been mounted, it is today often led to an open vessel (capsule, plastic, glass vessel) or a collection bag.

When the fluid has been removed, installation of other fluid can be an advantage. If the cavity is infected, rinsing by addition of saline and the subsequently remove it again is often recommended. By subsequent aspiration and rinsing this procedure results in a dilution of the residual volume and the bacteria therein.

Further, supply or injection of medicine, like cortisone after removal of fluid in a joint is a well-known procedure. When medicine has to be injected the dead volume of injection part has to minimal compared to the drug volume, in order to dose the medicine correctly.

Another example is injection of fluid or air to resolve a blockage in the needle, the drain tube or catheter.

When using a hypodermic needle on a syringe the emptying of the fluid is impeded, inter alia because the syringe, which is mounted on the hypodermic needle, needs to be removed several times with a view to emptying the fluid suctioned. If a three-way tap has been mounted, the said three-way tap needs to be alternated between suction and emptying position, simultaneously with the mounted syringe being actively pulled out in order to suck the fluid and subsequently being pushed in with a view to emptying the syringe through an outlet, which is generally led through some sort of hose to an open vessel (capsule, plastic! glass vessel) or a collection bag, e.g. of plastic. Finally, the outlet hose must also be handled in relation to the outlet. When emptying fluid after breast surgery (seroma collection) it is often advantageous to be two persons. One of the persons performs the suction by holding the plunger handle of the syringe out whilst the other person uses the hand to move the fluid towards the spot, where the hypodermic needle has penetrated the skin. Outside this the assistant can ensure that the collecting hose is kept in a right position. The procedure done by two persons allows a more complete emptying without penetrating the skin several times and thus limits the risk of infection.

The procedures, as it is generally performed today, for emptying fluid or air from cavities below skin level can be divided into:

A. Hypodermic Needle Mounted on a Syringe
1. Introducing the hypodermic needle into a cavity with fluid or air.
2. Fixing the puncture needle in a certain position and often with a certain desired depth of the needle tip below the skin.
3. Pulling back the plunger handle of the syringe with a view to filling the syringe with fluid/air from the cavity.
4. Separating the syringe and the hypodermic needle.
5. Emptying the contents of the syringe into the collection vessel (capsule, plastic/glass vessel)
6. Assembling the hypodermic needle and the syringe again.
7. Repeating the suction of fluid or air from the cavity.
8. Repeating the procedure in item 3-7 until all fluid or air has been sucked from the cavity.

B. Hypodermic Needle Mounted on a Syringe with a Three-Way Tap
1. Introducing the hypodermic needle into a cavity with fluid or air.
2. Fixing the puncture needle in a certain position with a certain depth of the needle tip below the skin.
3. Pulling back the plunger handle of the syringe with a view to filling the syringe with fluid/air from the cavity.
4. Turning the three-way tap away from initial position. Pushing down the plunger handle of the syringe in order to empty the contents of the syringe into the collection vessel: capsule, plastic/glass vessel, or collection bag.
5. Turning the three-way tap back to initial position with a view to repeating the procedure as mentioned in item 3-5.
6. Repeating the procedure in tem 3-5 until all fluid or air has been sucked from the cavity below the skin.

These procedures may be difficult to perform by a single person, especially when the system has to be separated when performing the procedures. (A item 3-7). This may result in incomplete emptying of fluid or air as well as non-observance of the aseptic procedure, e.g. backflow of fluid or air from the hypodermic needle into the cavity, with a subsequent higher risk of infections. In addition, handling of the evacuated fluid in open vessels is both unhygienic and unpleasant for the patients to experience.

The procedure for emptying and rinsing of the cavity below skin level, as it is generally performed today, is as follow:

C. Hypodermic Needle, a Syringe and a Saline Bag Mounted on with a Three-Way Tap:

1. Turn the three-way valve such that there is connection between the needle and syringe and closed for the saline inlet.
2. Introducing the hypodermic needle into a cavity with fluid or air.
3. Fixing the puncture needle in a certain position with a certain depth of the needle tip below the skin.
4. Pulling back the plunger handle of the syringe with a view to filling the syringe with fluid/air from the cavity.
5. Separating the syringe and the hypodermic needle.
6. Emptying the contents of the syringe into the collection vessel (capsule, plastic/glass vessel)
7. Assembling the hypodermic needle and the syringe again.
8. Repeating the suction of fluid or air from the cavity.
9. Repeating the procedure in item 3-7 until all fluid or air has been sucked from the cavity.
10. Turning the three-way tap away from initial position onto a position where there is connection between the saline bag and needle.
11. Open the tubing clamp on the saline tubing line a let saline into the cavity.
12. Repeat the procedure 1 to 9.
13. Repeating the procedure item 1-12 until an appropriate rinsing of the cavity has been obtain, typically observed when the removed fluid is clear.

Patients with arthritis have often fluid accumulation in their joints. This fluid is often removed to relief pain and to prevent further fluid accumulation injection of medicine, eg cortisone is often added.

The procedure for emptying and adding medicine of the cavity below skin level, as it is generally performed today, is as follow:

D. Hypodermic Needle, a Empty Syringe and Syringe with Medicine:

1. Assemble the needle and empty syringe.
2. Introducing the hypodermic needle into a cavity with fluid or air.
3. Fixing the puncture needle in a certain position with a certain depth of the needle tip below the skin.
4. Pulling back the plunger handle of the syringe with a view to filling the syringe with fluid/air from the cavity.
5. Separating the syringe and the hypodermic needle.
6. Emptying the contents of the syringe into the collection vessel (capsule, plastic/glass vessel)
7. Assembling the syringe with medicine on the hypodermic needle
8. Inject the medicine
9. Remove needle Improved clamping devices are needed also in other types of medical appliances, such as in irrigation systems for rectal irrigation, bladder irrigation and the like.

The documents U.S. Pat. No. 4,053,135, U.S. Pat. No. 4,643,389, U.S. Pat. No. 6,196,519, U.S. Pat. No. 3,419,245, U.S. Pat. No. 4,369,951, U.S. Pat. No. 2,309,302, U.S. Pat. No. 5,230,704 and U.S. Pat. No. 4,435,170 disclose examples of known tube clamps. However, these are all complicated to use and produce, and/or provide inadequate clamping.

SUMMARY OF THE INVENTION

In view of the above mentioned need, a general object of the present invention is to provide an apparatus comprising a conduit clamping device which alleviates the above-discussed problems of the prior art, and at least partly fulfils the above-discussed needs.

This and other objects are achieved with an apparatus comprising a conduit clamping device according to the appended claims.

According to a first aspect of the invention there is provided an apparatus comprising a conduit clamping device with a closing mechanism for closing and opening passage of fluid or air in a flexible conduit. The apparatus comprises:

a) a movable arm or disk that is connected to a knob;
b) a conduit in form of a tube, that is laid flat against an abutment or protrusion; and
c) a guide structure that constrains the movable arm or disk between the guide structure and the tube and designed such that movement of the arm or disk will control the compression of the tube.

The terms "conduit" and "tube" are in the following used to indicate a structure enclosing a lumen, and being made of at least somewhat flexible material. The cross-sectional shape is preferably circular, but other shapes, such as oval, may also be provided.

The term "knob" is used to indicate a gripping element which is manually operable. The knob may have a circular or rectangular shape, but many other shapes are also feasible.

The present invention provides a conduit clamping device which is easy to integrate in various types of apparatus. It is also cost-efficient to manufacture, and easy to use. In particular, it provides easy control for the user, allowing the user to manipulate the clamping device by means of a control arm or a knob, e.g. by means of only one finger, such as the thumb. Further, the clamping device provides distinct positions corresponding to fully closed and fully opened. The clamping device may also easily be made biased so that these positions will be obtained more easily. Still further, a very low force is required for manipulation and control.

The present invention differs from previously known clamping devices inter alia in that by using the knob or manipulation arm as control allows for better control of the handle. As the medical procedure controlled by the clamping device may take several minutes, e.g. a compression of a handle will give stress in the hand in order to overcome the spring force closing mechanism. Further, the clamping device of the present invention is made of very few parts, which makes it easy and cost-efficient to manufacture and assemble. The apparatus may also be made as completely disposable, thereby avoiding the problems associated with cleaning and sterilization of reusable equipment.

Further, the movable arm preferably has an abutment end facing the tube or conduit, which moves laterally towards the tube/conduit, and preferably in a direction essentially normal to the longitudinal direction of the tube/conduit. Hereby, a very efficient transfer of movement is provided. Further, the abutment end is preferably tapered in the direction towards the tube/conduit, and preferably to provide a relatively distinct and sharp edge.

For example, the invention provides a design of a for tubing clamping device, that can be built into an apparatus for removal and an apparatus which enables penetration of intact skin in order to suck and add fluid from a closed cavity into a vessel during one single procedure and without changing or separating the individual parts. For example, this may be obtained by connecting the hypodermic needle with the mouth of a handle and by connecting the said hypodermic needle with a first end of a conduit, the other end of which is connected to the suction and collection device, and by the handle having a closing mechanism, which co-operates with the conduit and which is activated by movement of a knob belonging to the handle.

The use of a hypodermic needle, which is appropriately sharp, in combination with the handle enables a relatively easy and controlled penetration of intact skin. The handle may e.g. be provided with a pistol-like handle, which provides the user with a good grip on the apparatus due to the pistol-like handle, and in addition the activation of the knob by e.g. a thumb enables an effective controlling of the suction process.

The handle further enables a relatively precise positioning of the needle tip both as regards direction and depth of penetration in relation to the underlying tissue, and additionally the user can use the other hand to work the skin area in question and push fluid forward to the needle tip. Thus, it is possible to establish vacuum in the cavity and thereby keeping the surfaces together, so that an acceleration of the adhesion of the surfaces in question may be possible, if so desired. During the extraction of the hypodermic needle it is still possible to maintain suction at the needle tip and thus ensure that vacuum is left in the cavity. The said procedure is simple, controllable and repeatable so that the emptying of fluid or air from the cavity may be performed in the same way each time and by a single person by use of the apparatus according to the invention. The apparatus may be formed as a closed system with vacuum, and the parts of which do not require separation during use, and thus the risk of backflow of fluid or air into the cavity of the patient during the treatment is reduced and thus also the risk of infection. The closed system also means that malaise due to the smell of the fluid is reduced. The knob of the handle may be operated by the thumb and enables both control of the motion of the hypodermic needle and control of flow rate of the fluid or air through the conduit.

According to an embodiment, the closing mechanism can be a flat stick, which is brought to a closing position by a 90 degree movement of the knob. This enables a very simple and economical production of the closing mechanism. This closing principle also provides a guillotine type of closing, where the moveable arm/disk moves in an essentially normal direction towards the conduit. This decreases the resistance to closing provided by the conduit, and ensures that a minimal operating force is required.

Further, the device can include a valve that allows for external communications of fluid and air. Thus, a particularly simple mechanism for removal and addition of fluid or air is obtained in connection with a hose connection between the hypodermic needle and the suction and collection device. By position of the valve close to the hypodermic needle, low loss of medicine is obtained due to the minimal dead volume obtain by this configuration.

Further, when the conduit is a flexible hose with one end directly connected to the hypodermic needle and the other end connected to the suction and collection device, and in addition the tube clamping mechanism build into the handle, a particularly reliable and controllable apparatus is obtained. Hereby, it is ensures that an especially tight connection between the hypodermic needle and the suction and collection device is obtained.

Appropriately, the hypodermic needle can, according to the invention, also be removably connected to the mouth of the handle via a Luer coupling.

According to an embodiment of the invention the tube clamping device can include a fixed abutment for the hose in the handle, whereas the knob is placed on a flat part of the handle and can be pushed into an inactivated or activated position. Thus, an especially simple closing mechanism is obtained in connection with a hose connection between the hypodermic needle and the suction and collection device.

Further, according to an embodiment of the invention, the vacuum vessel can have a closable inlet stub, through which the vacuum vessel is connected to the other end of the hose, so that backflow is avoided.

According to one alternative, the guide structure is formed by a solid wall or top of the apparatus. The solid wall or top preferably has the form of a handle, as has been discussed in more detail in the foregoing.

According to another alternative, the guide structure may be formed as an elongate channel, and wherein the arm or disk comprises a pin extending into said channel, and thereby being guided by said channel during movement. Preferably, the guide structure is formed as a first elongate channel, and wherein the arm or disk comprises a second elongate channel, and wherein the knob or manipulation arm comprises a pin extending into said channels, and thereby controlling movement of said movable arm or disk. The disk or arm is preferably pivotable around a pivot, preferably fixed to the apparatus, and wherein an abutment end is arranged at a distance from said pivot.

The movement of the movable arm or disk is preferably arranged to be biased into two separate positions. Such biasing may be obtained in various ways. For example, a spring, and preferably a spring plate, may be arranged to bias the knob position into two positions. Alternatively, at least one of the elongate channels may be curved, thereby biasing movement of the moveable arm or disk. The first elongate channel is preferably essentially linear, and wherein the second elongate channel is curved into a concave shape, as seen from the abutment or protrusion.

The movement of the movable arm or disk is preferably arranged to be biased into a fully closed and a fully opened position, respectively. The biasing also ensures that no inadvertent movement between different positions occurs, since some resistance against moving position is provided.

As discussed previously, a vacuum source may be connected to the conduit.

The arm or disk is preferably integrally connected to the knob or manipulation arm. Most preferably, the arm or disk and the knob or manipulation arm are formed by a single, and unbroken piece of material.

The knob is preferably manoeuvrable by means of one finger, e.g. by the thumb. In case of a manipulation arm, it is however also possible to manipulate the manipulation arm by means of an electric motor, which is electrically controllable by the user.

As has been discussed in the foregoing, the apparatus is useable for removal and supply of fluid or air, below skin level, at a human or an animal, such as being useable for removal of accumulations of fluid or air being a result of e.g. surgery, or solely accumulations of fluid in e.g. knees or other tissue with cavity or in regions of organs, e.g. gastrointestinal regions or in the heart/lungs.

However, the conduit clamping device is also useable in other medical appliances, such as in irrigation systems, e.g. for rectal irrigation or bladder irrigation.

A system, and preferably a portal system, for rectal irrigation or bladder irrigation may comprise:
  a reservoir for an irrigating liquid;
  a probe for arrangement in a user;

one or several pumps, such as an electrical pump or manual pump, for directly or indirectly pumping irrigation liquid from the reservoir to the probe; and a control unit for controlling the transfer of said irrigation liquid;

tubing providing fluid communication between said reservoir, control unit and probe.

The probe preferably comprises an inflatable retention element, such as an inflatable balloon. The balloon may be inflatable by the same pump(s) as used for pumping irrigation liquid, or by one or several separate pump(s).

The above-discussed clamping device is preferably integrated in the control unit, but may alternatively be placed at other parts of the system. The clamping device may be arranged to control at least one of the following tubes/conduits:

a tube/conduit leading from the reservoir to the probe;

a tube/conduit leading from a pump to the reservoir, in order to provide a controlled overpressure in the reservoir in case of indirect pumping;

a tube/conduit leading from a pump to inflatable balloon on the probe; and a tube/conduit leading from the inflatable balloon on the probe for deflation.

The clamping device is preferably biased to assume one of two distinct positions, and preferably a fully opened and a fully closed position, as has been discussed in the foregoing.

The clamping device of the present invention is particularly suited for systems of this type, since it can be operated very easily, which is particularly advantageous for users with reduced dexterity, and users who lack strength in their hands.

The knob or manipulation arm is preferably accessible from the surface of the control unit. This makes it easy to access the pump with one hand only. Typically with this arrangement, it is e.g. possible to operate the knob or manipulation arm one finger, e.g. the thumb. This provides a very convenient and precise controllability of the irrigation system. Alternatively, the manipulation arm may be controlled electrically, e.g. by means of an electric motor. For example, the manipulation arm may be connected to an internal electric servo, linear motor or the like within the control unit housing, and be controllable from the outside by some control element. Thus, the control unit may comprise a button or the like, which may be used to control the electric motor.

Preferably, the control unit further comprises at least one further control element, such as a control button, arranged on the surface of the housing for operating the control switch(es). The control elements may be realized as a areas on a touch screen.

However, alternatively or additionally, the control element(s) may be arranged on a separate control, connected e.g. by an isolated wire to the control unit. Hereby, the control can be made small, and easy to use and handle. The control may also be wirelessly connected to the control unit, and thereby function as a wireless remote control. For example, a smart phone, tablet computer, laptop computer or the like may comprise an application/software which makes it useable as a remote control for the irrigation system.

The pump(s) may be arranged to pump irrigation liquid from the reservoir to the probe directly or indirectly. By direct pumping is here meant that the pumping is made directly on the irrigation fluid. Such a pump may e.g. be arranged in-line in a conduit leading from the reservoir to the probe. By indirect pumping is here meant that the pumping is made on a different fluid, such as air, which when pumped exerts a pressure to the irrigation fluid, whereby the irrigation fluid is also pumped. For example, the first pump may be arranged to pump a gas, and preferably air, into the reservoir to create a pressure in the reservoir to displace the irrigation liquid therefrom and feed it to the probe.

It is further preferred that the control unit is arranged at a distance from both the reservoir and the probe, and being connected to the reservoir and probe, respectively, through the tubing. This makes it possible to have the reservoir at a distance from the control unit, e.g. on the floor, and still provide a good working position for the user.

The control unit is preferably programmable. For example, the control unit may be programmable to set at least one of: total irrigation liquid volume to be discharged and irrigation liquid discharge flow rate.

For inflation of the balloon, any fluid may be used. For example, it is possible to connect the pump to the reservoir, and use irrigation liquid for filling of the balloon. It is also possible to provide a separate supply of another fluid, liquid or gas, for filling of the balloon. However, preferably ambient air is used for inflation of the balloon.

A manually operable pump is very cost-efficient, which lowers the overall costs of the product. Further, a manually operable pump provides a very precise controllability for the user, which is useful for example for the very limited fluid volume needed for adequate inflation of the retention member/balloon, and considering the importance of the balloon being inflated with precision. Too low inflation may result in a too weak fixation, which may result in the probe falling out during irrigation. Too high inflation may be painful and even potentially harmful to the user. However, similar precise control may be achieved by means of an electric pump, which may be arranged to pump at low flow rates and with very precise control.

One or several valves may also be arranged to release fluid from the retention member, and/or to release overpressure from the reservoir. One or several of these valves may be realized as the above-discussed conduit clamping device. When air is used as a filling fluid for the retention member/balloon, the valve for releasing fluid from the balloon may open up to a vent channel. The valve is in this embodiment closed by default, and opened up whenever the balloon filling fluid is to be released. If e.g. irrigation liquid is used, the valve may instead release the irrigation liquid back to the reservoir or into the probe for discharge during irrigation. However, it is also possible to release the fluid from the balloon into a drain compartment or the like. In a preferred embodiment, the control unit comprises a valve for releasing fluid from the retention member for deflation.

According to another aspect of the present invention, there is provided a use of the irrigation device as discussed above for rectal irrigation.

According to another aspect of the invention there is provided a conduit clamping device for closing and opening passage of fluid or air in a flexible conduit, comprising:

a housing;

a pivotable element, pivotable around a pivot connected to said housing, and having a protruding closing end;

a conduit in the form of a tube;

an abutment fixedly connected to said housing, wherein the conduit is arranged between the abutment and the protruding closing end;

a first elongate channel being arranged in said housing;

a second elongate channel being arranged in the pivotable element;

a pin extending through said first and second elongate channels and being displaceable within said channels; and a manipulation arm or knob connected to said pin, for displacement of said pin within said channels;

whereby the first and second elongate channels are arranged to provide movement of said protruding closing end towards and away from said abutment upon displacement of said pin.

Hereby, similar advantages as discussed above in relation to the first aspects are obtainable. Further, the same additional features are useable in this aspect of the invention.

Preferably, at least one of said elongate channels is curved, thereby biasing movement of the moveable arm or disk.

Further, the first elongate channel is preferably essentially linear, and wherein the second elongate channel is curved into a concave shape, as seen from the abutment.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein:

FIGS. 11a and 11b show the control unit of FIG. 10 in more detail, and with some components being removed for improved visibility. The clamping device is here shown in opened position. FIG. 11a shows the control unit from below, with the back wall being removed, and FIG. 11b shows the control unit from the forward side.

FIGS. 13a and 13b shows the elongate channels of the clamping device in more detail. In FIG. 13a, the same arrangement and view as in FIG. 12a is shown, whereas FIG. 13b shows an identical view as in FIG. 13a, with the only exception that the movable element of the clamping device has been removed, for improved visibility.

DETAILED DESCRIPTION OF PREFERRED EMBODIMENTS

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Figure 1:
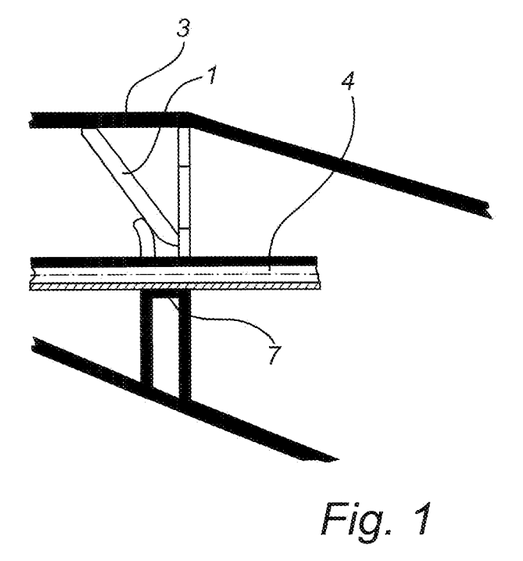
FIG. 1 schematically illustrates tubing clamping design according to an embodiment of the invention in an open position.

The apparatus illustrated in FIG. 1 comprises a tube clamping device in an open position and which comprises a movable disk 1, a solid top 3, and a conduit in form of a tube 4, that is laid flat against a protrusion 7.

Figure 2:
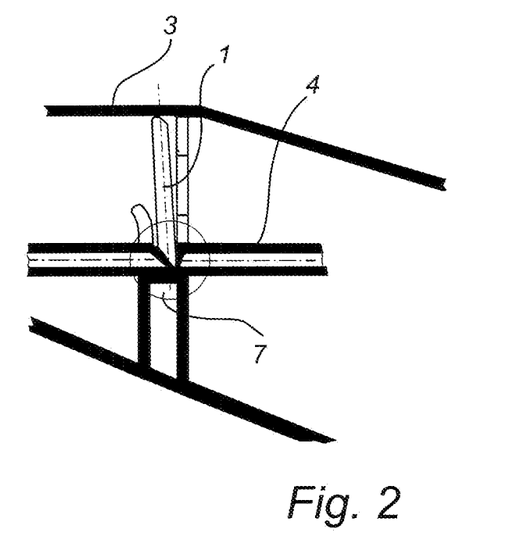
FIG. 2 schematically illustrates tubing clamping design according to the embodiment of FIG. 1 in a closed position.

The apparatus illustrated in FIG. 2 comprises a tube clamping device in an closed position and which comprises a movable disk 1, that is compressed against a solid top 3, and a conduit in form of a tube 4, that is laid flat against a protrusion 7.

Figure 3:
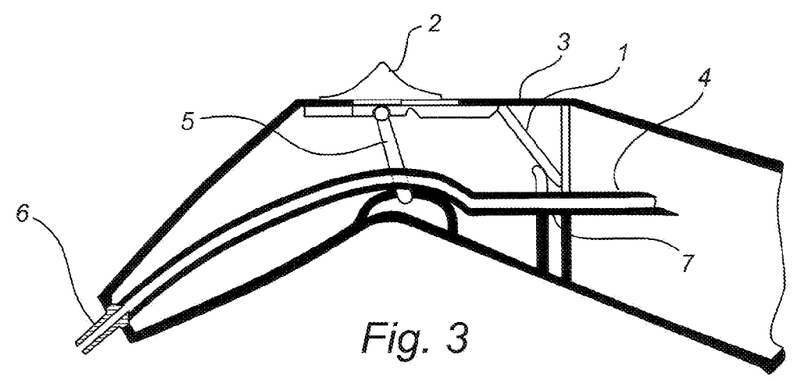
FIG. 3 schematically illustrates an apparatus for removal of fluid or air below skin level in accordance with an embodiment of the invention in an open position.

The apparatus illustrated in FIG. 3 comprises a pistol-like handle, and which comprises a grip 3, a knob 2, comprises a movable disk 1, a solid top 3, a conduit in form of a tube 4, that is laid flat against a protrusion 7, and a barrel 6. A plate 5 is placed under the knob 2 and the bottom part of the handle. In the shown position the plate 5 will keep the knob shown in the current shown position. At the front end of the barrel a hypodermic needle can be mounted, the said hypodermic needle being connected via a Luer coupling 6 to a hose 4, which partly extends through the barrel 4 of the handle 1 and passes out and is connected to a vacuum vessel.

The vacuum vessel may be of a commonly known type such as the one described in U.S. Pat. No. 4,376,439, said document hereby incorporated in its entirety by reference. The handle in FIG. 3, is made of an appropriate plastic material and the main body is prepared form 2 separate parts and is constructed so as to be fixed with the other part by a snap connection, which has not been illustrated in details. The knob and the luer connection in the barrel end can both be fixated in the main body during snapping together the parts the main body is constructed from.

The apparatus describe can also be made without the plate 5 as the movable disk 1 will be held in the open position by friction. The conduit can be placed behind or through a hole in the plate 5

Figure 4:
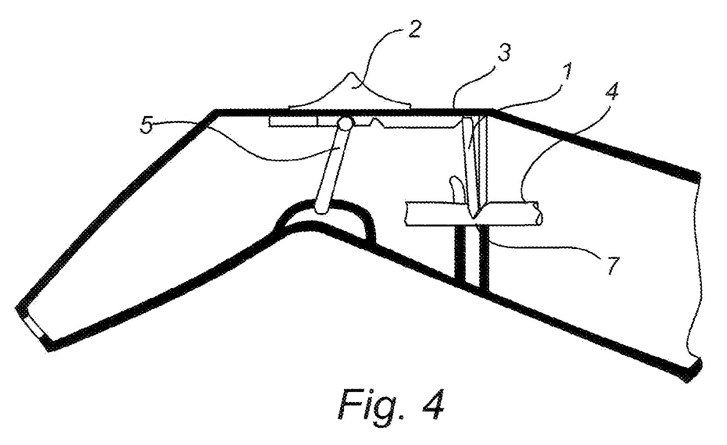
FIG. 4 schematically illustrates the apparatus for removal of fluid or air below skin level of FIG. 3 in a closed position.

The apparatus illustrated in FIG. 4 comprise the handle seen in FIG. 3 in a closed position. When the knob 3 is moved in horizontal direction on the flat part of the grip 3, the disk 1 is moved in direction against the abutment 7. This is resulting in a protrusion of the hose being pushed up against an abutment 7. By this, the passage through the hose 7 is closed between the disk and the abutment. When the knob 2 is moved from the position shown in FIG. 3 to the position in FIG. 4, the plate 5 will be bend in the middle position and after passing the middle position, be forced into the closed position. The disk 5 will therefore act as spring that will keep the knob in either the open or closed position.

The apparatus describe can also be made without the plate 5 as the movable disk 1 will be held in the closed position by friction.

When activating the knob 3, i.e. by pressing the knob 3, so that it is moved towards the barrel end, the hose 7 is released from the clamping and the passage is opened.

When using the apparatus the user grips around the handle 3 and maneuvers the hypodermic needle through the skin into the cavity from which the fluid or the air is to be removed. The grip of the handle enables an easy handling of the apparatus with one hand while the other hand is available for working the surrounding areas of the skin and the cavity in question. The vacuum in the vacuum vessel is easily connected to the inner hypodermic needle and thus the cavity in question by activation of the knob 2, so that fluid is sucked out, which is transferred to the vacuum vessel through the hose 4. By means of the apparatus according to the invention, the treatment is performed in a closed system during the entire process, the system operating with a vacuum, which is independent from other vacuum sources and delivered only together with the vacuum vessel. When it is desired to terminate the flow of the fluid and the air through the tube 4, the knob 3 merely has to be moved to the closed position.

The handle may have many different shapes and may be formed in different ways.

Figure 5:
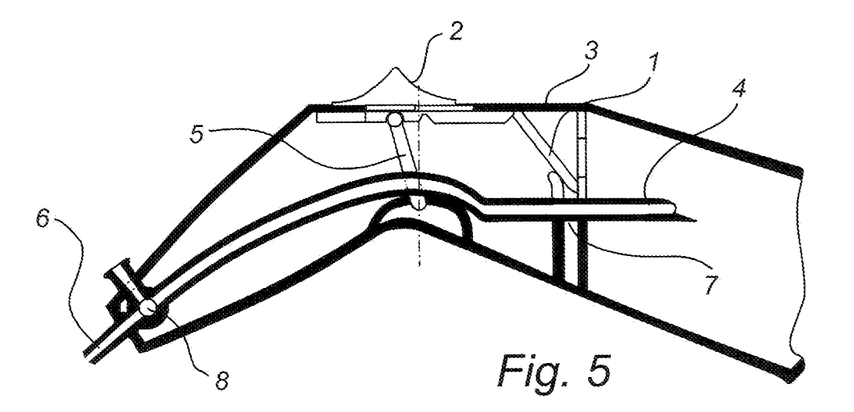
FIG. 5 schematically illustrates an apparatus for removal or supply of fluid or air below skin level in accordance with an embodiment of the present invention in an open position and with the valve in closed position.

The apparatus illustrated in FIG. 5 comprises a handle shown in FIG. 3 with the addition of a valve 8 in the barrel end. In FIG. 5 the valve 8 is in such a position that allows for flow from the luer 6 through the tube 4, when the knob 2 is in the open position as shown in FIG. 3.

Figure 6:
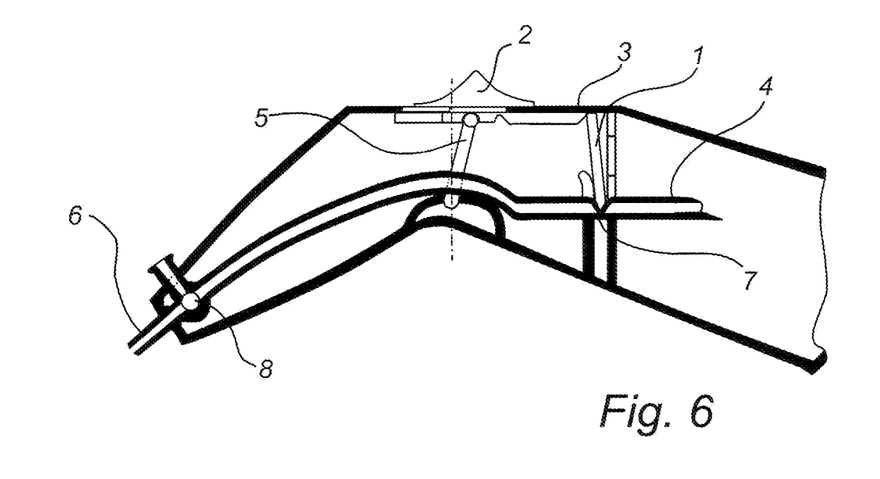
FIG. 6 schematically illustrates an apparatus for removal or supply of fluid or air below skin level of FIG. 5 in a closed position and the valve in an open position.

The apparatus illustrated in FIG. 6 comprises a handle shown in FIG. 5 with the valve 8 is in such a position that allows for flow from the luer 6 through the inlet port in valve 8 and with the knob 2 in closed position.

The apparatus described in FIG. 5 and FIG. 6 can be used for both aspirations of fluid and addition of fluid or air.

An example of the use of the apparatus is removal of fluid from an infected cavity.

Before position of the needle in the cavity, a saline bag is connected to the valve 8 by a tube. After placing the needle in the cavity, the fluid is removed. Then the knob is moved to the closed position and the valve 8 is turned to open the connection between the needle and the saline bag and thereby allowing saline to flow into the cavity. After and appropriate volume of saline is in the cavity, the valve is turned back to allow for aspiration by moving the knob 2 to the open position. This procedure can be repeated several times and by this action, the cavity is being rinsed.

Another example of the use of the apparatus is removal of fluid from a swollen joint.

Before position of the needle in the cavity, a syringe with medicine, eg cortisone, is connected to the valve 8 by a luer connection. After placing the needle in the cavity, the fluid is removed. Then the knob is moved to the closed position and the valve 8 is turned to open the connection between the needle and the syringe and thereby allowing the medicine to be injected into the cavity. After the medicine has been injected into the cavity, the valve is turned back to allow for aspiration. During removal of the needle, it is possible to remove fluid or medicine the channel in the skin made by the needle and thereby removing residual medicine in the channel.

Another example of the use of the apparatus is removal of fluid from a cavity. Before position of the needle in the cavity, a syringe with air or saline, is connected to the valve 8 by a luer connection. During aspiration of the fluid, the needle can be blocked.

Figure 7:
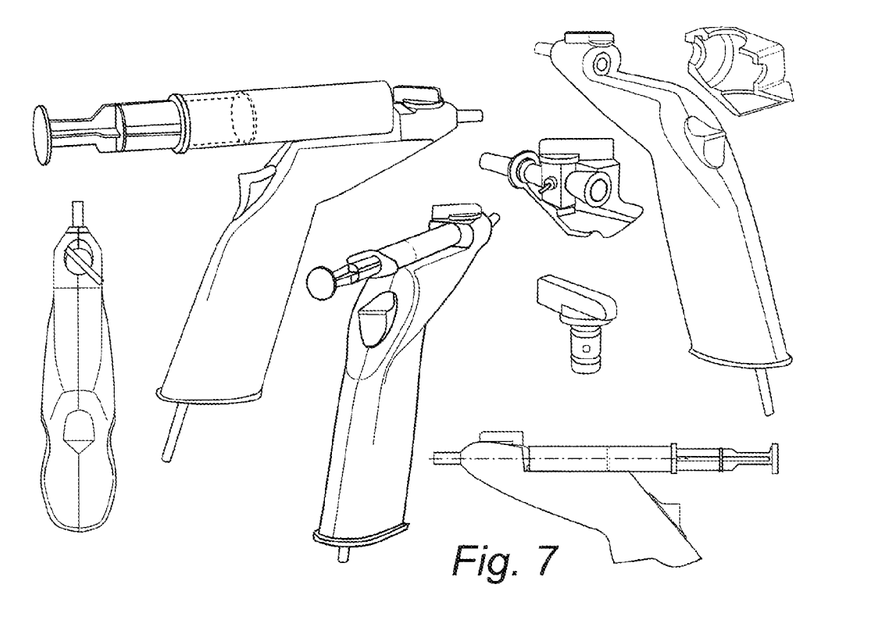
FIG. 7 schematically illustrates an apparatus for removal or supply of fluid or air below skin level in accordance with an embodiment of the present invention in preferred configurations.

Then the knob is then moved to the closed position and the valve 8 is turned to open the connection between the needle and the syringe and thereby allowing the air or saline to be injected into the needle and clear the blockage. After the needle blockage has been cleared, the valve is turned back to allow for aspiration FIG. 7 schematically illustrates an apparatus for removal or supply of fluid or air below skin level in preferred configurations for a convenient placing of syringes.

The illustrated valve device is only illustrated schematically and may have many different shapes.

The apparatus has been described with reference to the preferred embodiments. Many changes can be made without deviating from the idea of the invention. E.g. the hypodermic needle 5, or a drain tube or a catheter, can be fixed to the pistol-like handle, and the individual parts can be made of such materials that they are disposable.

However, alternative realizations of the conduit clamping device are feasible, and also, the apparatus are useable for other types of medical appliances. In the following, an irrigation system, particularly useful for rectal irrigation, will be discussed, in relation to an alternative embodiment of the clamping device. However, it is to be acknowledged by the skilled reader that any of the discussed clamping devices may be used in both systems, and also in other systems intended for other types of irrigation, aspiration and the like.

Figure 8:
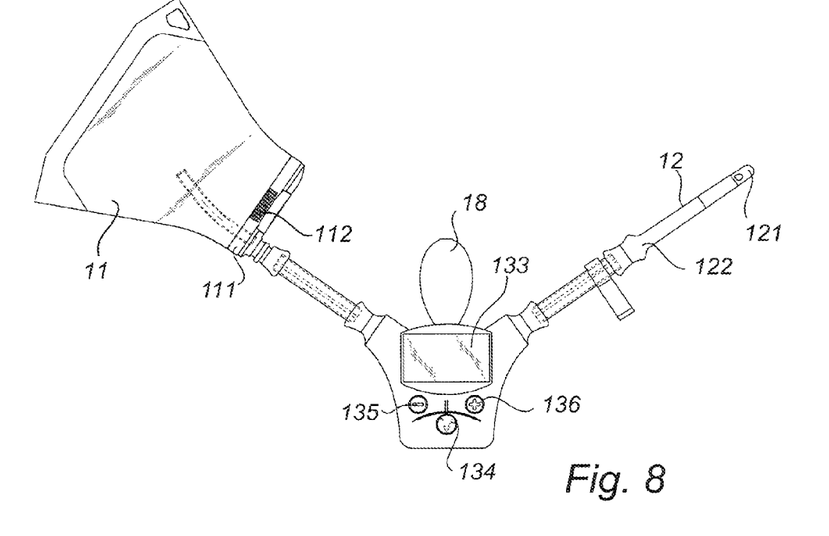
FIG. 8 schematically illustrates an apparatus for rectal irrigation in accordance with an embodiment of the present invention.

FIG. 8 discloses an irrigation system according to a first exemplary embodiment, comprising a reservoir 11 for an irrigating liquid, a probe 12 for arrangement in a user, and a control unit 13.

The reservoir may be realized in various ways. For example, the reservoir may be formed by a rigid, semi-rigid or flexible material. In case a semi-rigid or flexible material is used, the reservoir may be collapsible or foldable, to make the irrigation system more compact prior to use. The reservoir is provided with an opening, closed by a lid, for filling of the reservoir. Tubing connecting the reservoir to the rest of the irrigation system may be provided through the lid, or through other access points on the reservoir.

In order to render the irrigation system as portable as possible, the container preferably has a capacity of less than 5 liters, more preferred less than 3 liters and most preferred less than 2 liters. If however the system is to be used for repeated irrigation, a larger capacity container may be necessary.

The probe 12 is provided with a retention member, such as an inflatable balloon 121, for fixing the catheter in a body cavity. Further, the probe may be provided with a rearward enlarged part 122, providing an abutment to hinder too deep insertion. The probe is provided with two lumens—one lumen for transfer of irrigation liquid through the probe, for discharge at the forward end, and one lumen for inflation and deflation of the balloon.

An electric or manual pump 14 for pumping irrigation liquid is provided. Here, the electrical pump 14 is arranged within the control unit 13. However, the pump may also be arranged outside the bounds of the control unit.

The control unit is here realized as a unitary, hand-held unit. The control unit comprises a display 133, and three control elements 134, 135 and 136. The control element is preferably realized as a depressible control button.

In this embodiment, a second pump 18 is arranged to pump fluid into the balloon of the probe. The pump is a manually operable pump. However, other types of pumps are also feasible. In the shown example, the manually operable pump is a bulb pump, comprising an inlet, provided with a one-way valve, allowing a fluid to enter but not exit the pump. Further, the pump comprises a pumping compartment and outlets, provided with a one-way valve, allowing a fluid to exit but not enter the pump. The pumping compartment is made of a resilient, squeezable material, which retains it shape when unloaded. By squeezing the pumping compartment, the fluid is pumped out through the outlet, and when the squeezing is relieved, the pumping compartment retains its original shape, thereby sucking in fluid through the inlet. In the illustrative example, the pump is used to pump air. Thus, the second pump 18 pumps air into the balloon 121 for inflation. The air is releasable through a valve (not shown).

Tubing is arranged to connect the reservoir, control unit and probe together. Preferred materials for the bulb pumps and the balloon can be any suitable material e.g. such as PVC, latex, TPE or PU. However, other materials providing similar properties can likewise be used.

Figure 9:
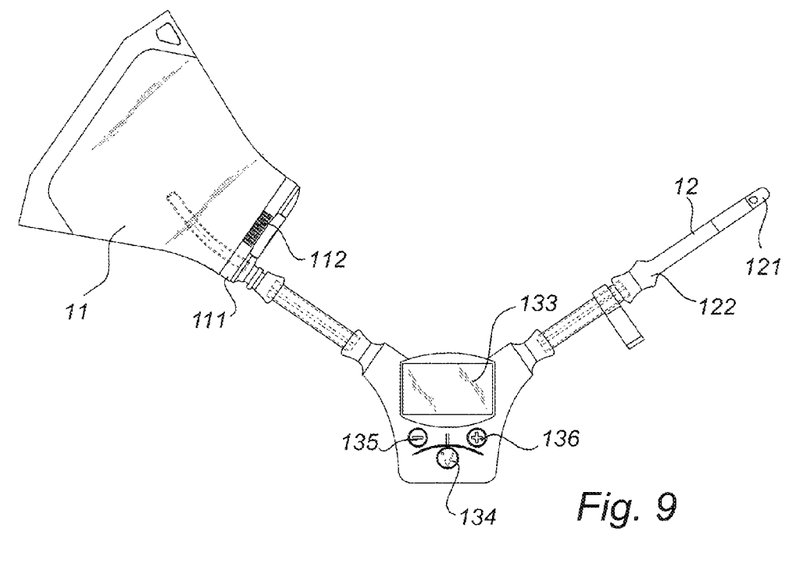
FIG. 9 schematically illustrates an apparatus for rectal irrigation in accordance with another embodiment of the present invention.

The second embodiment, illustrated in FIG. 9, resembles the above-described first embodiment. However, here the first pump 14 is also useable to inflate the balloon 121 of the probe. Consequently, there is no need for the second pump 18.

The irrigation liquid can be any liquid which is capable of irrigation the body cavity of interest. In order to stimulate bowel movements suitable irrigation liquids includes water, hypertonic aqueous salt solutions, solutions or suspensions of cathartic agents, such as bisacodyl or phenolphthalein, and mineral oil.

The clamping arrangement is preferably arranged within the control unit 13.

Figure 10:
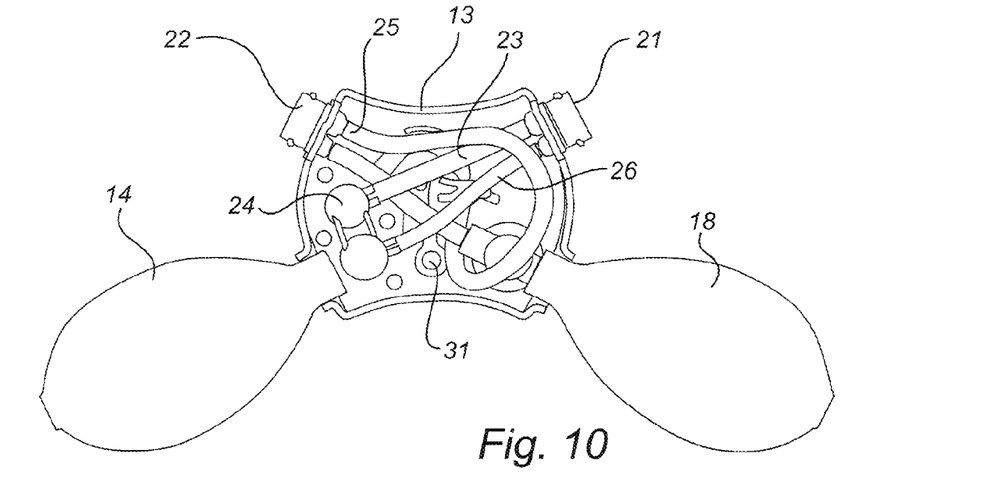
FIG. 10 a control unit of an embodiment of the present invention, e.g. useable in a rectal irrigation system, wherein a back wall of the housing has been removed for improved visibility.

An exemplary embodiment of the control unit is shown in more detail in FIGS. 10-13. As best seen in FIG. 10, the control unit is provided with an access port 21 to the irrigation liquid reservoir, and an access port 22 to the probe. A first tube 23 connects the access port 21 to an optional non-return valve 24. A second tube 25 connects the non-return valve to the access port 22, through the clamping arrangement. A third tube 26 connects the pump 14 to the access port 21. Hereby, air may be pumped into the irrigation liquid reservoir through the third tube 26, creating an overpressure in the irrigation liquid reservoir. As a consequence, liquid is pumped through tubes 23 and 25 to the probe. The control unit is preferably enclosed within a housing.

The clamping device of this embodiment will now be discussed in more detail. However, as discussed in the foregoing, this or similar clamping devices may also be arranged at other positions, to control other tubes, and may also be used in other types of medical appliances.

Figure 11A:
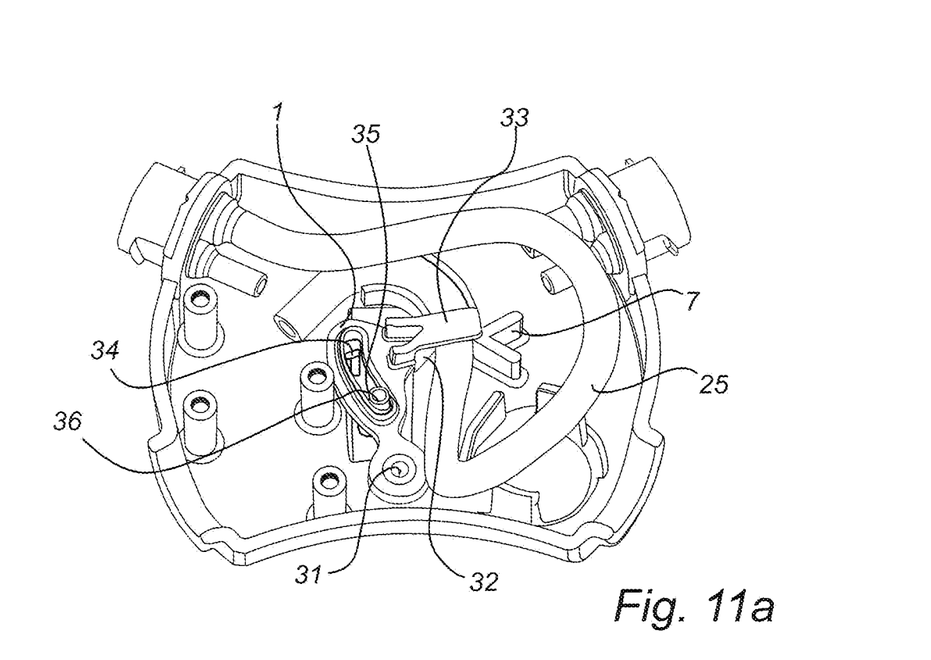

The clamping device comprises a movable element 1, as seen in e.g. FIG. 11a. Here, the movable element comprises a pivotable element, pivotable around a pivot 31, fixedly connected to the housing of the control unit housing. The movable element further comprises a protruding closing end 32, arranged at a distance from the pivot 31. The protruding closing end 32 is preferably provided with a tapering end, forming a relatively sharp edge towards the conduit and abutment 7. The abutment 7 is preferably also provided with a relatively sharp edge towards the conduit. The protruding closing end 32 may further be provided with a stabilizing protrusion 33 extending past the conduit at one or both sides of the conduit. Hereby, the conduit is maintained in place during opening and closing.

The movable element 1 further comprises an elongate channel 34. This channel is a closed channel, and is preferably arranged between the protruding closing end 32 and the pivot 31. A further fixed elongate channel 35 is preferably provided. This elongate channel is preferably arranged within the housing of the control unit. Further, a pin 36 is provided to extend through the elongate channels 34, 35. The pin 36 is displaceable, and movement of the pin creates a movement of the movable element 1, thereby causing the protruding closing end 32 to move towards or away from the abutment 7.

For manipulation of the pin 36, the pin may be connected to a knob or handle 2, arranged on the outside of the control unit housing. Alternatively, the pin may be connected to a manipulation arm (not shown) being operable by an electric motor.

Preferably, one of the channels 34, 35 is curved, to provide bias of the movable element into two distinct positions, and preferably a fully closed and a fully opened position, respectively. Preferably, the fixed channel 35 is arranged in an essentially straight disposition, and preferably arranged in the same direction as the conduit to be clamped. The movable channel 34 is preferably arranged in a curved disposition, and preferably being curved into a concave shape as seen from the abutment 7. Hereby, the moveable arm or disk is biased to the end positions.

Figure 11B:
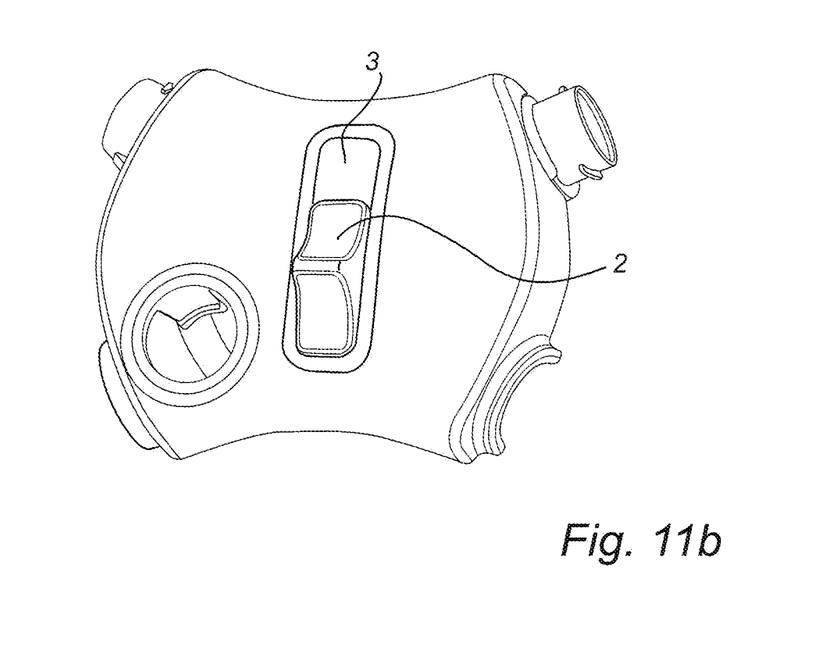
Figure 12A:
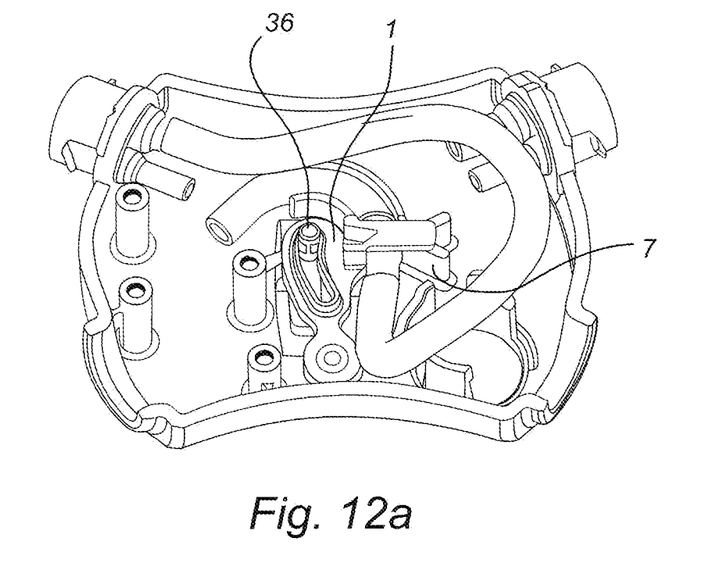
FIGS. 12a and 12b show the same control unit and views as in FIGS. 11a and 11b, respectively, but where the clamping device has been moved to a closed position.
Figure 12B:
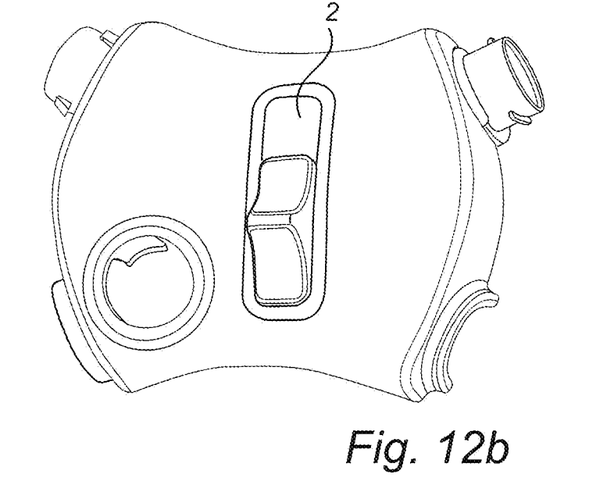
Figure 13A:
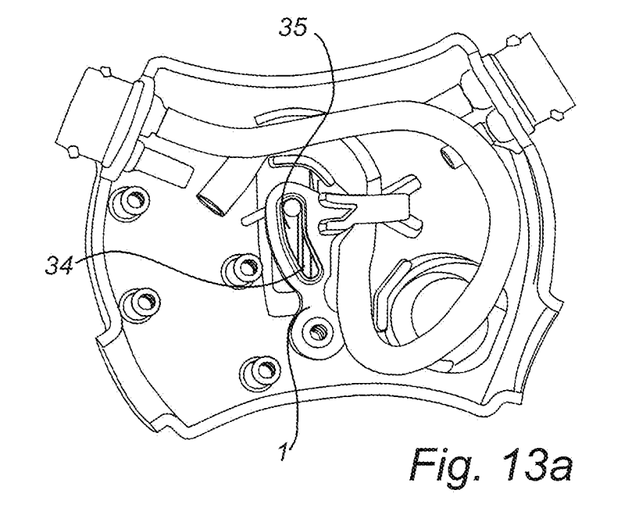
Figure 13B:
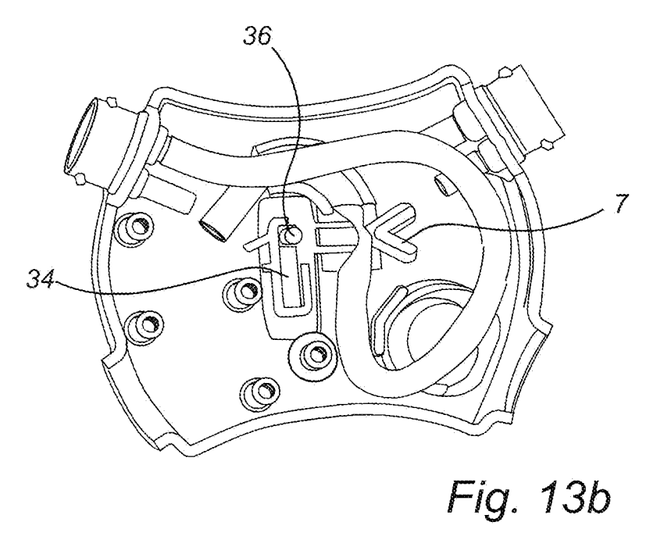

FIGS. 11a and 11b shows the clamping device in an open position, whereas FIGS. 12a and 12b show the clamping device in a closed position. FIGS. 13a and 13b show the elongate guiding channels in more detail.

The person skilled in the art realizes that the present invention is not limited to the preferred embodiment. For example the movable element may have various shapes, and be movable in different ways. Further, the clamping device is usable in many types of medical appliances.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. An apparatus comprising a conduit clamping device with a closing mechanism for closing and opening passage of fluid or air in a flexible conduit, wherein the apparatus includes:
   a housing;
   a movable arm or disk, disposed in the housing and connected to a manipulation arm or a knob;
   an abutment or protrusion extending from said housing;
   a conduit in the form of a tube that is laid flat against said abutment or protrusion; and
   a guide structure that constrains the movable arm or disk to movements between said guide structure and the tube and that is designed such that movement of the arm or disk will control the compression of the tube.

2. The apparatus according to claim 1, wherein the guide structure is formed by a solid wall or top of the apparatus.

3. The apparatus according to claim 2, wherein the solid wall or top has the form of a handle.

4. The apparatus according to claim 3, wherein a valve is placed at a barrel end of the handle.

5. The apparatus according to claim 3, wherein a hypodermic needle, or a drain tube or a catheter, is connected to the barrel end of the handle.

6. The apparatus according to claim 3, wherein the hypodermic needle, or a drain tube or a catheter, is removably connectable to the mouth of the handle.

7. The apparatus according to claim 1, wherein the guide structure is formed as a first elongate channel, and wherein the arm or disk comprises a second elongate channel, and wherein the knob or manipulation arm comprises a pin extending into said channels, and thereby controlling movement of said movable arm or disk.

8. The apparatus according to claim 7, wherein the disk or arm is pivotable around a pivot, and wherein an abutment end is arranged at a distance from said pivot.

9. The apparatus according to claim 1, wherein the movable arm or disk is arranged to be biased into two separate positions.

10. The apparatus according to claim 9, wherein a spring, and preferably a spring plate, is arranged to bias the knob position into two positions.

11. The apparatus according to claim 9, wherein the first elongate channel is essentially linear, and wherein the second elongate channel is curved into a concave shape, as seen from the abutment or protrusion.

12. The apparatus according to claim 9, wherein the movement of the movable arm or disk, is arranged to be biased into a fully closed and a fully opened position, respectively.

13. The apparatus according to claim 1, wherein a vacuum source is connected to the conduit.

14. The apparatus according to claim 1, wherein the moveable arm or disk is integrally connected to the manipulation arm or knob.

15. The apparatus according to claim 1, wherein the knob is maneuverable by means of one finger.

16. The apparatus according to claim 1, further comprising a suction and collection device, wherein the suction and collection device is a vacuum vessel with a vacuum obtained in advance.

17. The apparatus according to claim 16, wherein the vacuum vessel has a closable inlet stub, through which the vacuum vessel is connected to a free end of the conduit.

18. The apparatus according to claim 1, wherein the apparatus is useable for at least one of the following: removal and supply of fluid or air, below skin level, at a human or an animal; removal of accumulations of fluid or air being a result of surgery; removal of accumulations of fluid in knees or other tissue with cavity; removal of fluid in regions of organs; removal of fluid in gastrointestinal regions; and removal of fluid in the heart/lungs.

19. The apparatus of claim 18, wherein the apparatus further comprises a hypodermic needle for penetration of the skin and a suction and collection device for suction of the fluid through the hypodermic needle, or a drain tube or a catheter.

20. The apparatus of claim 18, wherein the apparatus further comprises a device for adding fluid to the cavity with the purpose of infusion of medicine in the cavity or performing lavage of preformed cavity or as a result of prior surgery.

21. The apparatus of claim 1, wherein the apparatus is used in an irrigation system.

22. The apparatus according to claim 1, wherein the moveable arm or disk is held in a closed position by friction between the moveable arm or disk and the guide structure.

23. A conduit clamping device for closing and opening passage of fluid or air in a flexible conduit, comprising:
 a housing;
 a pivotable element, pivotable around a pivot connected to said housing, and having a protruding closing end;
 a conduit in the form of a tube;
 an abutment fixedly connected to said housing, wherein the conduit is arranged between the abutment and the protruding closing end;
 a first elongate channel being arranged in said housing;
 a second elongate channel being arranged in the pivotable element;
 a pin extending through said first and second elongate channels and being displaceable within said channels; and
 a manipulation arm or knob connected to said pin, for displacement of said pin within said channels;
 whereby the first and second elongate channels are arranged to provide movement of said protruding closing end towards and away from said abutment upon displacement of said pin.

24. The conduit clamping device according to claim 23, wherein at least one of said elongate channels is curved, thereby biasing movement of the moveable arm or disk.

25. The conduit clamping device according to claim 23, wherein the first elongate channel is essentially linear, and wherein the second elongate channel has a concave profile.

* * * * *